(12) United States Patent
Cluzel et al.

(10) Patent No.: US 7,330,255 B2
(45) Date of Patent: Feb. 12, 2008

(54) TOTAL INTERNAL REFLECTION FLUORESCENCE APPARATUS

(75) Inventors: Philippe Cluzel, Chicago, IL (US); Sebastien Harlepp, Selestat (FR)

(73) Assignee: University of Chicago, Chicago, IL (US)

( * ) Notice: Subject to any disclaimer, the term of this patent is extended or adjusted under 35 U.S.C. 154(b) by 175 days.

(21) Appl. No.: 11/008,002

(22) Filed: Dec. 9, 2004

(65) Prior Publication Data

US 2006/0126063 A1 Jun. 15, 2006

(51) Int. Cl.
*G01J 3/30* (2006.01)
*G01N 21/64* (2006.01)

(52) U.S. Cl. .................................. 356/318; 250/458.1

(58) Field of Classification Search ............... 356/317, 356/318
See application file for complete search history.

(56) References Cited

U.S. PATENT DOCUMENTS 3,999,855 A * 12/1976 Hirschfeld ................. 356/338
6,055,106 A     4/2000 Grier et al.
7,154,602 B2   12/2006 Wachsmuth

OTHER PUBLICATIONS

Chattrapiban, et al., "Generation of nondiffracting Bessel beams by use of a spatial light modulator," *Optics Letters* 28(22):2183-2185 (2003).

Grosjean, et al., "Immaterial tip concept by light confinement," *Journal of Microscopy* 202(2):273-278 (2001).
Starr, et al., "Total Internal Reflection with Fluorescence Correlation Spectroscopy: Combined Surface Reaction and Solution Diffusion," *Biophysical Journal* 80:1575-1584 (2001).
Tao, et al., "Experimental study of holographic generation of fractional Bessel beams," *Applied Optics* 43(1):122-126 (2004).
"Total Internal Reflection Fluorescence Microscopy," Olympus BioSystems GmbH (2 pages) (2002).
"ConfoCor 2 Making Fluorescence Correlation Spectroscopy (FCS) available to the Life Scientist" [online](printed Oct. 2004) (42 pages).
Cluzel, et al., "An ultrasensitive bacterial motor revealed by monitoring signaling proteins in single cells," *Science* 287:1652-1655 (2000).
Dufresne, et al., "Computer-generated holographic optical tweezer arrays," *Review of Scientific Instruments* 72(3):1810-1816 (2001).
Elson, et al., "Fluorescence Correlation Spectroscopy, I. Conceptual Basis and Theory," *Biopolymers* 13:1-27 (1974).

(Continued)

*Primary Examiner*—F. L. Evans
(74) *Attorney, Agent, or Firm*—Marshall, Gerstein & Borun LLP

(57) ABSTRACT

Techniques are provided for illuminating a sample by using total internal reflection (TIR) from a diffraction limited focused annular illumination beam. The illumination forms an affected region and an overlapping confocal region that may have dimensions the below 1 μm. An adjustable diffractive optical element, for example, may create a second order Bessel profile laser beam that is focused on a sample using a high-numerical aperture objective under TIR. An evanescent field excites fluorescent biological material in the confocal region, and fluorescence from the material is analyzed in fluorescence correlation spectroscopy system.

73 Claims, 7 Drawing Sheets

OTHER PUBLICATIONS

Grier, "A revolution in optical manipulation," *Nature* 424:810-816 (2003).

Grosjean et al., "Bessel beams as virtual tips for near-field optics," *Journal of Microscopy* 210:319-323 (2003).

Janicki et al,. "From silencing to gene expression: real-time analysis in single cells," *Cell* 116:683-698 (2004).

Korn, et al., "Gene expression analysis using single molecule detection," *Nucleic Acids Research* 31(16):1-8 (2003).

Ladavac, et al., "Sorting mesoscopic objects with periodic potential landscapes: optical fractionation," Department of Physics, James Franck Institute and Institute for Biophysical Dynamics, The University of Chicago, Chicago, Illinois 60637 (Dated: May 26, 2004) pp. 1-4.

Levene, et al., "Zero-mode waveguides for single-molecule analysis at high concentrations," *Science* 299:682-686 (2003).

Magde, et al., "Fluorescence Correlation Spectroscopy. II. An Experimental Realization," *Biopolymers* 13:29-61 (1974).

Magde, et al., "Thermodynamic fluctuations in a reacting system-measurement by fluorescence correlation spectroscopy," *Physical Review Letters* 29(11):705-708 (1972).

Paulsson, "Summing up the noise in gene networks," *Nature* 427:415-418 (2004).

Prieve, "Measurement of colloidal forces with TIRM," *Advances in Colloid and Interface Science* 82:93-125 (1999).

Thompson, et al., "Total internal reflection fluorescence: applications in cellular biophysics," *Current Opinion in Biotechnology* 8:58-64 (1997).

Thompson, et al., "Recent advances in fluorescence correlation spectroscopy," *Current Opinion in Structural Biology* 12:634-641 (2002).

Webb, "Fluorescence correlation spectroscopy: inception, biophysical experimentations, and prospectus," *Applied Optics* 40(24):3969-3983 (2001).

Durnin, "Exact-Solutions for Nondiffracting Beams. 1. The Scalar Theory," *J Opt Soc Am A* 4(4):651-654 (1987).

Kinjo, et al., "Ultrasensitive hybridization analysis using fluorescence correlation spectroscopy," *Nucleic Acids Research* 23(10):1795-1799 (1995).

Thompson, et al., "Measuring Surface Dynamics of Biomolecules by Total Internal Reflection Fluorescence with Photobleaching Recovery or Correlation Spectroscopy," *Biophys J*, vol. 33, pp. 435-454 (1981).

Vasara, et al., "Realization of General Nondiffracting Beams with Computer-Generated Holograms," *J Opt Soc Am A* 6(11):1748-1754 (1989).

Zhuang, et al., "Enzymatic activity and folding of single RNA molecules," *Faseb J* 14(8):A1587 (2000).

Zocchi, "Mechanical measurement of the unfolding of a protein," *Europhysics Letters* 35(8):633-638 (1996).

Bacia et al., "Fluorescence Correlation Spectroscopy Relates Rafts in Model and Native Membranes," *Biophysical Journal* 87:1034-1043 (2004).

Bacia et al., "Probing the Endocytic Pathway in Live Cells Using Dual-Color Fluorescence Cross-Correlation Analysis," *Biophysical Journal* 83:1184-1193 (2002).

Bose et al., "The Mobility of Phytochrome within Protonemal Tip Cells of the Moss *Ceratodon purpureus*, Monitored by Fluorescence Correlation Spectroscopy," *Biophysical Journal* 87:2013-2021 (2004).

Chattopadhyay et al., "Measuring Unfolding of Proteins in the Presence of Denaturant using Fluorescence Correlation Spectroscopy," *Biophysical Journal* 88:1413-1422 (2005).

Foldes-Papp et al., "A New Dimension for the Development of Fluorescence-Based Assays in Solution: From Physical Principles of FCS Detection to Biological Applications," *Exp. Biol. Med.* 227:291-300 (2002).

Haupts et al., "Dynamics of fluorescence fluctuations in green fluorescent protein observed by fluorescence correlation spectroscopy," *Proc. Natl. Acad. Sci. USA* 95:13573-13578 (1998).

Kim et al., "Intracellular calmodulin availability accessed with two-photon cross-correlation," *Proc. Natl. Acad. Sci. (USA)* 101(1):105-110 (2004).

Li et al., "Measuring single-molecule nucleic acid dynamics in solution by two-color (filtered ratiometric fluorescence correlation spectroscopy," *Proc. Natl. Acad. Sci. (USA)* 101(40):14425-14430 (2004).

Ruan et al., "Spatial-Temporal Studies of Membrane Dynamics: Scannning Fluorescence Correlation Spectroscopy (SFCS)," *Biophysical Journal* 87:1260-1267 (2004).

Rusu et al., "Fluroescence Correlation Spectroscopy Studies of Peptide and Prtein Binding to Phospholipid Vesicles," *Biophysical Journal* 87:1044-1053 (2004).

Schwille et al., "Fluorescence correlation spectroscopy reveals fast optical excitation-driven intramolecular dynamics of yellow fluorescent proteins," *Proc. Natl. Acad. Sci. (USA)* 97(1):151-156 (2000).

Schwille et al., "Fluorescence Correlation Spectroscopy" Biophysics textbook online, Chap. 2, pp. 1-33, (2000) http://www.biophysics.org/btol/.

Stella et al., "Aggregation and Water-Membrane Partition as Major Determinants of the Activity of the Antibiotic Peptide Trichogin GA IV," *Biophysical Journal* 86:936-945 (2005).

* cited by examiner

300

302

304

TOTAL INTERNAL REFLECTION FLUORESCENCE APPARATUS

FIELD OF THE DISCLOSURE

The present disclosure relates generally to fluorescence techniques and, more specifically, to fluorescence techniques employing evanescent fields created by total internal reflection.

BACKGROUND OF RELATED ART

For many years, researchers have used spectroscopy and microscopy techniques to identify biological materials within a sample. The techniques typically involve applying a light to a sample and then analyzing the fluorescence light emitted from that sample, where the emitted light may be compared to known characteristic spectra data to identify the biological material in the sample. Traditionally, researchers used these techniques to measure static values, such as the overall concentration of a biological material within a sample.

More recently, as biological study has matured, researchers have developed a need for moving beyond static measurements toward making real-time measurements of intracellular molecular events in living cells. That is, researchers have developed a need for real-time spectroscopy and microscopy techniques. For example, it has become increasingly important to develop non-invasive experimental approaches of monitoring molecular activities of biological complexes in living cells. With real-time measurements researchers could measure such molecular activities, which would help researchers examine sub-micron and nano-metric biological complexes. With nano-metrically sized biological complexes (e.g., clusters of receptors, protein-RNA, protein-DNA associations, RNA-RNA, DNA-DNA and cells), it is desirable to be able to monitor and characterize the associations and functions of isolated biological complexes, and preferably with visually representative data. This desire to monitor associations and functions of isolated biological complexes is not only important in living cells, but is also important for in vitro experiments, such as protein binding assays and RNA or DNA microarrays, for example. Yet, despite the need for monitoring techniques capable of resolving phenomena at molecular or intracellular levels, present spectroscopy and microscopy techniques are insufficient.

Although introduced nearly thirty years ago, researchers have recently started using fluorescence correlation spectroscopy (FCS) to resolve small-scale associations and functions in biological samples. The techniques are capable of fluorescence detection over small detection volumes, approximately the size of E. coli. Fluorescence correlation spectroscopy offers quantitative information by analyzing the spontaneously fluctuating fluorescence intensity obtained from diffusing fluorescent molecular complexes, thus, allowing for real-time measurements.

In implementation, however, these conventional FCS techniques use a wide-field evanescent wave to illuminate a sample. And although some success has been reported, these techniques are limited in the size of the sample being tested. By using wide-field evanescent waves, such as those created by total internal reflection from a transversely-propagating laser beam, overly large sample volumes are illuminated. These volumes result from the disperse intensity profile of wide-field evanescent waves, which exhibit a Gaussian profile. In FCS systems, these large sample volumes present a number of problems for researchers.

One problem is that, because of the overly large FCS detection volumes, the sample volume tested will have a large number of contaminants. Thus, in measuring biological complexes such as membrane protein activities or receptor clusters, these large sample volumes will not only contain the molecules being measured but also large numbers of contaminant molecules, which represent noise in spectroscopy measurements. And in current FCS systems, this noise may be large enough to prevent accurate measurement of biological complexes below a certain dimensional size.

An example conventional FCS technique is that of the ConfoCor 2 system from Carl Zeiss, Inc. of Germany, which measures the concentration and the diffusion of fluorescent molecules using FCS. The FCS detection volume of the ConfoCor 2 system has reported dimensions over a micron in length (1.5 µm) along the Z axis, which means an FCS detection volume that is much larger than the typical size of a protein complex, which is about 100 nm. Such large volume systems are likely to be too noisy for accurate measurements of smaller-sized biological materials.

TIR (total internal reflection) illumination combined with FCS presents a bleaching problem, as well. Bleaching is the destruction of a portion of a sample due to the high intensity of the light source illuminating the sample during spectroscopy. In conventional wide-field TIR the entire field of view is illuminated, which causes bleaching outside the region of detection.

SUMMARY OF THE INVENTION

In accordance with an example described herein, apparatuses and techniques are described for providing more efficient FCS than that of conventional FCS techniques. Techniques are described for reducing the FCS detection volume, e.g., by decreasing the dimensions along a Z axis. The dimensions may be decreased below 1000 nm to approximately the size of a typical nano-cellular organelle, i.e., about 100 nm, or below. This decrease may be achieved, for example, by forming an annular illumination beam and focusing that beam into a substrate under a condition of TIR. The TIR creates a confined evanescent field extending above the substrate thereby forming an affected region of a biological, chemical, pharmaceutical or other material disposed on the substrate over which fluorescence will occur.

In an example, spatially ultra-resolved TIR imaging is used to illuminate small objects or fluorescent molecules in a nano-metric volume. In some examples, the detection volume may be characterized by a light spot radius of about 200 nm (in an XY plane) or below and by a tunable penetration depth ranging from 50 nm to 1000 nm. The techniques may be combined with FCS in order to measure concentration and binding affinities of fluorescent molecules with a high spatial resolution. Similar applications are possible to characterize binding activities of fluorescent molecules onto nano-organelles within individual live cells.

In accordance with an example, provided is an illumination apparatus comprising: a laser source for providing a reference laser beam; a diffractive optical element positioned to receive the reference laser beam and convert the reference laser beam into an annular illumination beam; and an optical objective positioned to couple the annular illumination beam into an optical substrate to produce an evanescent wave above the optical substrate.

In accordance with another example, an apparatus is provided for exciting a material disposed on an optical substrate, the apparatus comprising: a laser source for providing a reference laser beam; a optical element positioned to receive the reference laser beam and convert the reference laser beam into an annular illumination beam; and an optical objective having an axis substantially normal to an entrance face of the optical substrate, the optical objective positioned to focus the annular illumination beam into the optical substrate and to produce an evanescent wave having an confocal region with a penetration depth into the material of 1000 nm or less.

In accordance with another example, provided is a method of exciting fluorescence in a material, the method comprising: coupling a reference laser beam into a diffractive optical element to convert the reference laser beam into an annular illumination beam propagating along an axis; focusing the annular illumination beam onto an optical substrate via an optical objective aligned along the axis; forming an, evanescent field extending above the optical substrate, the evanescent field forming an affected region; and forming a confocal region in the affected region, the confocal region having a penetration depth extending into a sample of the material positioned at an exit face of the optical substrate.

In accordance with another example, provided is a method of measuring a biological function of an affected region of a material disposed on an optical substrate, the method comprising: coupling a reference laser beam into a diffractive optical element; converting the reference laser beam into an annular illumination beam propagating along an axis; focusing the annular illumination beam onto the optical substrate via an optical objective aligned along the axis; forming an evanescent field extending above the optical substrate, the evanescent field forming the affected region; forming a confocal region in the affected region, the confocal region having a penetration depth extending into the material; collecting fluorescence from the confocal region; and correlating the fluorescence collected from the confocal region with the biological function of the material.

In accordance with another example, provided is a method of measuring a biological function of a material, the method comprising: forming an annular illumination beam propagating along an axis; focusing the annular illumination beam into an optical substrate; forming an evanescent wave extending above the optical substrate, the evanescent wave forming an affected region; forming a confocal region in the affected region and with a penetration depth into the material of 1000 nm or below; collecting fluorescence from the confocal region; and correlating the fluorescence from the confocal region with the biological function of the material.

Although the techniques are described with respect to example applications, the techniques are not limited thereto and may be used in other applications including high-resolution imaging, microarray assays, DNA mapping, in addition to spatio-time resolved spectroscopic techniques, such as FCS. Furthermore, by way of example not limitation, the illumination apparatus may be used in other applications, such as lithography, data storage, or laser writing, where an affected region created by an evanescent wave may be used as a virtual tip, probe, or other sub-micron confined laser energy source.

DETAILED DESCRIPTION OF EXAMPLES

Figure 1:
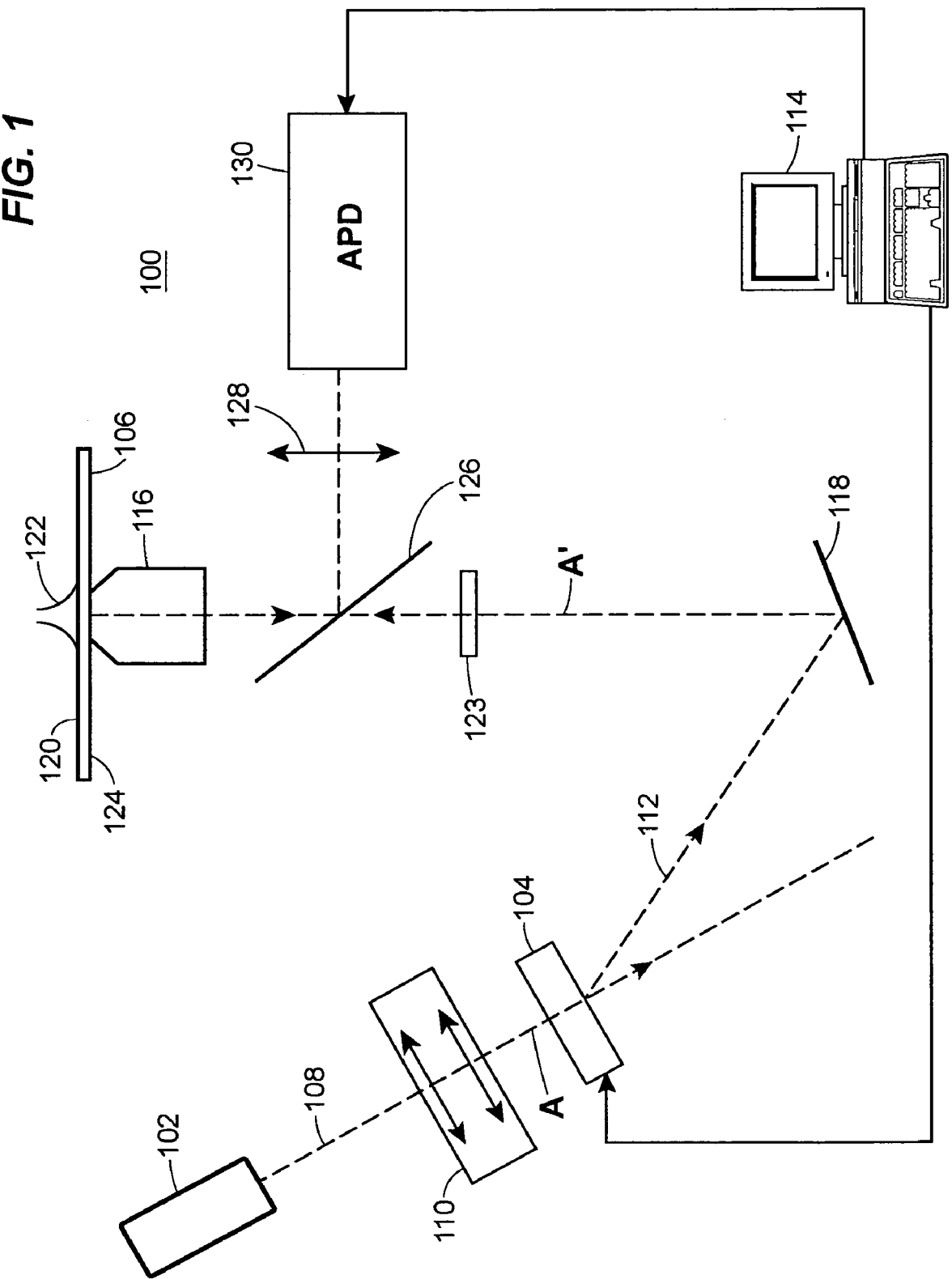
FIG. 1 illustrates an illumination apparatus including a diffractive optical component capable of forming an annular illumination beam.

An illumination apparatus 100 that may be used in fluorescence correlation spectroscopy is illustrated in FIG. 1. The apparatus 100 includes a laser source 102 that provides an input laser beam and a diffractive optical element (DOE) 104 that may alter that input beam in a desired manner to produce an affected beam that may be focused into an optically transparent substrate 106. By way of example, the laser source 102 may be a sapphire laser producing a laser beam at a blue wavelength, e.g., 400 to 500 nm; although, the laser source is not limited to any particular wavelength range. Furthermore, the laser source 102 may be a dedicated laser, as shown, or the source 102 may be another source of laser energy, such as a laser amplifier, optical element or waveguide. The substrate 106 may be slide, container, microarray or other optical element.

In the illustrated example, the laser source 102 produces a reference laser beam 108 that is coupled to a first telescoping optical element 110 to expand the reference beam 108 before coupling to the DOE 104. For example, the beam width of beam 108 may be expanded to cover the entire DOE 104. In the illustrated example, the DOE 104 receives the reference laser beam 108 and converts the reference laser beam into an annular illumination beam 112.

To create the annular illumination beam 112, in the illustrated example, the DOE 104 may be a dynamically changeable diffractive component, such as a computer-generated hologram. The DOE 104, for example, may present an adjustable hologram to the reference beam 108 (either through transmission as shown or, in other examples, through a reflective DOE) to create a desired profile on the annular illumination beam 112. In some examples, the DOE 104 is a liquid crystal component imprinted with a computer-generated hologram, such as a liquid crystal display. The DOE 104 may be any spatial light modulator (SLM), however, including those that have an electrically-addressable phase mask component capable of converting the reference beam 108 into the annular illumination beam 112, such as a computer-addressable liquid crystal display. Although the DOE 104 is described in a preferred example as being adjustable, the DOE 104 may alternatively be a fixed diffractive optical element. The DOE 104 may represent other diffractive elements than those described and may include a combination of optical elements including one or more diffractive optical elements.

The DOE 104 is normal to an axis of propagation (A) of the reference beam 108, but other orientations are achievable. For example, light may be obliquely incident on the DOE 104.

Figure 2:
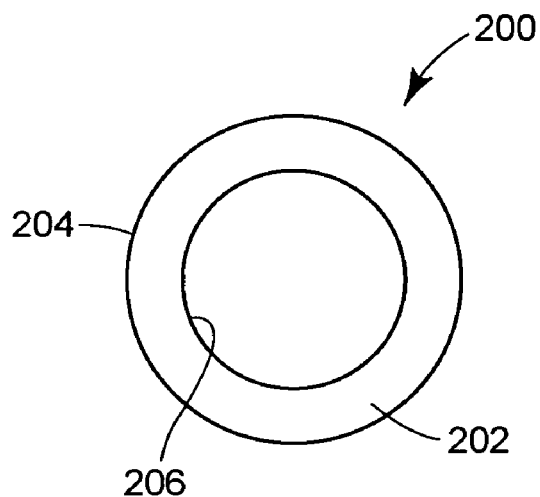
FIG. 2 illustrates an annular illumination beam created by the diffractive optical component of FIG. 1.

In the illustrated example, the DOE 104 is controlled by a computer 114 that sets the hologram or phase mask component of the DOE 104 to a desired pattern. The hologram or phase mask component, for example, may convert a Gaussian-profile reference beam into a second order Bessel-profile annular illumination beam as generally shown in FIG. 2. In the case of a liquid crystal,component as the DOE 104, the computer 114 may execute code to control pixels of the component to form the desired phase mask component.

As described in further detail below, with the DOE 104 as an adjustable optical element, the DOE 104 may still be statically used. For example, the DOE 104 may be adjusted once to set a desired hologram or phase mask component for producing a single annular illumination beam. Alternatively, the DOE 104 may be continuously or variably adjustable, to controllably alter the annular illumination beam.

To focus the annular illumination beam 112 into the substrate 106 under TIR and such that an evanescent field extends above the substrate 106, a high-numerical aperture optical objective 116 receives the beam 112, for example from an optional mirror 118, and focuses the beam 112 to a diffraction-limited spot in the substrate 106, for example, at an exit face 120 thereof. By focusing the annular illumination beam 112 at sufficiently high angles of incidence onto the inner boundary of the exit face 120, the annular beam 112 will experience total internal reflection and thereby produce an evanescent field 122 extending above the exit face 120. In various applications described below, a biological, chemical, pharmaceutical or other material (not shown) may be positioned on the substrate 106 and overlapping the evanescent field 122 to affect fluorescence in the material.

To create sufficiently high angles of incidence, the optical objective may have a numerical aperture (NA) of approximately 1.4 or higher, for example. In some examples, the NA may be bigger than the refraction index of the host material for a biological sample, e.g., higher than the host liquid which typically would have a refraction index of approximately 1.33. The higher the NA the larger the angles of incidence of the annular beam 112 into the substrate 106.

In some examples, when the annular beam 112 is circularly polarized, the beam 112 may be converted to a linear polarization, e.g., a TM polarization, using a polarizing element 123. The element 123 may represent a polarizer or polarizer in combination with a polarization rotator, for example. Polarization control is optional, however.

In the illustrated example, the objective 116 is aligned coaxially with a propagation axis (A') and normally to an entrance face 124 of the substrate 106. The evanescent field extends principally, normal to the exit face 120. The beam 112 may be incident along other angles of incidence, such as obliquely under total internal reflection, but that may prevent the formation of a diffraction limited spot.

Persons of ordinary skill in the art will appreciate that the guiding optical elements (i.e., the telescoping and mirror elements) are provided by way of example and may be eliminated, replaced, or augmented with additional optical elements, such as lenses, mirrors, prisms, an axicon and apertures to affect a desired beam shape or beam path, as desired.

The annular illumination beam 112 may contain light that is confined to an annular or partially-annular region over which the light may be focused into an optical substrate under TIR. For example, the annular illumination beam 112 may have a beam profile 200 (as shown in FIG. 2) that is a second order or higher Bessel profile. Only a primary first order ring 202 of the Bessel profile 200 is shown, but it will be known to persons of ordinary skill in the art that additional, attenuated higher order rings (not shown) may also exist. These orders may be removed by iris or aperture.

In the illustrated example, the first order ring 202 is bounded by an outer diameter 204 and an inner diameter 206. The inner diameter 206 encloses a dark core 208 of the Bessel profile 200, which corresponds to the portion of the profile 200 which would otherwise contain light that would be refracted through the exit face 120 of the substrate 106, and not totally internally reflected. By using the DOE 104 to convert the reference beam 108 to a higher order Bessel profile beam, i.e., an order higher than 1, effectively removing light from the region 208, no refraction of light will occur at the substrate 106. Instead, only an evanescent field will be formed. Furthermore, as described in further detail below, the shape of the Bessel profile (e.g., the distance of the inner diameter 206 or outer diameter 204) may be adjusted to alter geometric properties of the evanescent field, such as how far the field extends above the substrate 106, i.e., a penetration depth.

Figure 3:
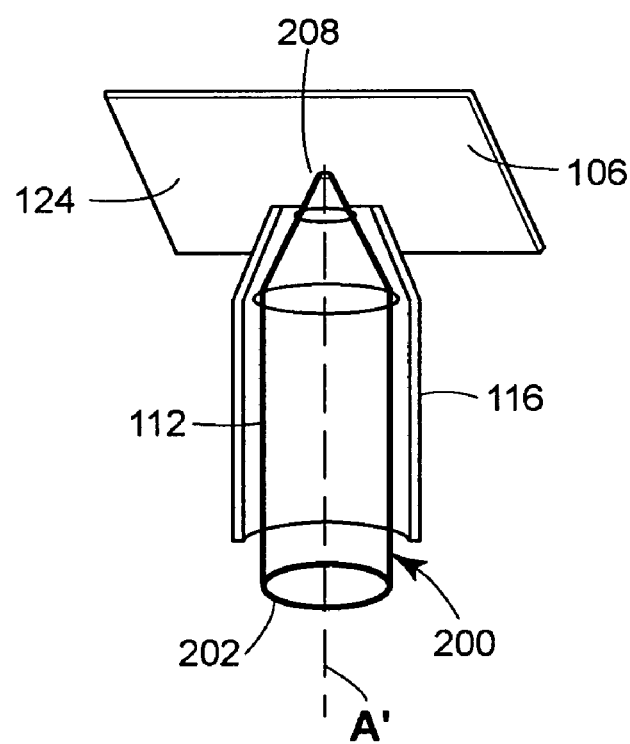
FIG. 3 illustrates the annular illumination beam of FIG. 2 as that beam is focused on an optical substrate under a total internal reflection condition to form an evanescent field.

Turning to FIG. 3, the substrate 106 is shown where the annular illumination beam 112 has been focused by the optical objective 116 (partially cut away) to a diffraction limited spot at a glass/solution interface of exit face 120. The objective 116 shares the axis A', which is normal to the entrance face 124. Using the reference numbers of FIG. 2, the annular region 202 is focused into the substrate 106 such that the light over the annular region 202 is incident upon the exit face 120 (not shown) at Brewster's angle or larger incidence for TIR. Because the beam 112 is annular, the resultant evanescent wave 122 is confined to a diffraction limited spot 208 (e.g., radius~200 nm). As a result, the annular beam results in a more confined evanescent wave over that of conventional TIR techniques for which the entire field of view would be illuminated, and for which an evanescent field would cover a much larger region.

It is noted that the annular illumination pattern of FIG. 2 is provided by way of example. Other Bessel profiles, including other even order Bessel profiles. (N=2, 4, 6 . . . n+2), and other annular profiles that can be focused to a diffraction limited spot for TIR may be used. Various Bessel profiles and corresponding phase masks for creating the same will be known to persons of ordinary skill in the art.

An illumination apparatus is now described by way of example, not limitation.

Example Illumination

The initial radius of a reference beam produced by a Coherent Sapphire 488-20 laser from Coherent, Inc. of Santa Clara, Calif. was magnified using a telescope in order to entirely cover the active area of a computer controlled SLM as the DOE, an LC2002 LCD available from Holoeye Photonics AG of Berlin Adlershof, Germany. The adjustable SLM was connected to a computer via a video board, a Matrox G450 PCI-video board available from Matrox Graphics Inc. of Quebec, Canada, to display a chosen phase mask profile. When the phase mask was illuminated with the laser beam, it produced a hologram shaped like a hollow tube of light deviated angularly from the zero-order beam.

For forming the phase mask, a scalar propagating field in a source free region z≧0 representing a laser beam profile was given by:

$$E(x, y, z \geq 0, t) = \exp[i(\beta z - \omega t)] \int_0^{2\pi} A(\phi) \exp[i\alpha(x\cos\phi + y\sin\phi)] \, d\phi. \quad (1)$$

A hologram of radius R was characterized by the complex amplitude function $t(\rho,\phi)=A(\phi) \exp[i(2\pi\rho/\rho_0)]$, where $\rho$ and $\phi$ were the cylindrical coordinates of the profile and where $\beta^2+\alpha^2=(\omega/c)^2=k^2$, k was the wave number and $A(\phi)$ was an arbitrary complex function of $\phi$. When $A(\phi)=\exp(in\phi)$, equation (1) became a Bessel function of the first kind of order n. In that case, $t(\rho,\phi)$ became a phase function of the form $t(\rho,\phi)=\exp[i\,\psi(\rho,\phi)]$ where:

$$\psi(\rho,\phi)=n\phi+2\pi\rho/\rho_0. \quad (2)$$

Figure 4A:
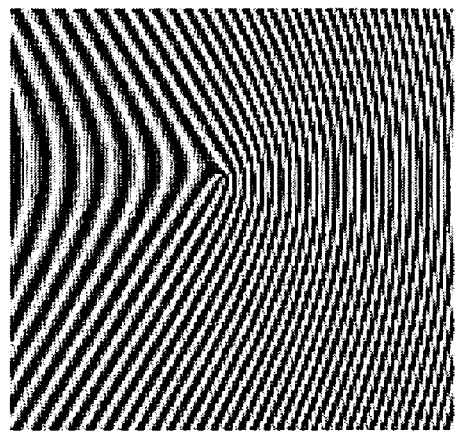
FIGS. 4A, 4B, and 4C illustrate an example phase mask of the diffractive optical component of FIG. 1 that may be used to create the annular illumination beam, an intensity profile of an annular illumination beam before being focused, and an intensity profile of an annular illumination beam after being focused, respectively.
Figure 4B:
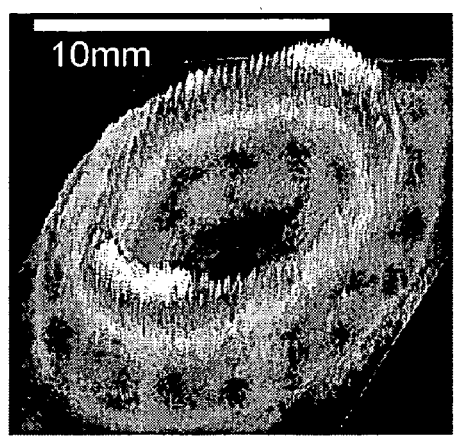
Figure 4C:
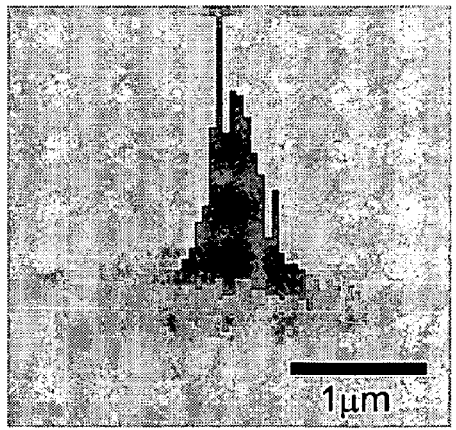

In order to construct an annular illumination beam deflected from the zero order, a phase mask component with the phase function given by the following formula was used:

$$\psi(\rho,\phi)=(\alpha\rho+n\phi+2\pi\nu\rho\cos\phi) \bmod[2\pi] \quad (3)$$

with $\alpha=(2\pi/\rho_0)$ and $\nu=\sin\gamma/\lambda$, $\gamma$ was the angle between the reference beam and the line normal to the surface of the adjustable SLM, wherein $\lambda$ was the wavelength of the reference laser beam and n was the order number, and wherein $\rho$ and $\phi$ were cylindrical coordinates of the phase mask component. The typical parameters used were $\alpha=2.8$, $n=2$ and $\nu=0.25$. A corresponding phase mask 300 that formed the annular illumination beam is shown in FIG. 4A. FIG. 4B illustrates an intensity profile 302 for the annular beam before focus, and FIG. 4C illustrates an intensity profile 304 after focus.

With the annular illumination beam formed from the phase mask, the annular illumination beam filled the back aperture of a high-numerical aperture objective (e.g., an Olympus Plan Apo TIRF x60 oil-immersion, high resolution 1.45 NA objective available from Olympus BioSystems of Planegg, Germany), which was used to generate the evanescent field illumination. The distance from the SLM to optical objective was around 3 meters, which was long enough to produce a well defined annular illumination beam. From the described implementation, it is recognized that higher orders of the Bessel beam could be eliminated with an iris so that only the first order ring fills the back aperture of the objective.

Returning to FIG. 1, the illumination apparatus 100 may be used in various applications, including in an FCS system that includes the objective 116, a dichroic mirror 126, a focusing element 128, and a photodetector 130, in the illustrated example. In an FCS system for example, the photodetector 130 may be a single photon counting device, such as an avalanche photodiode device, that is fast enough to resolve the diffusion times of the materials under examination in real time. For example, the photodetector 130 may have a black current counting rate of approximately 25-500 photon counts per second, and a signal count rate of between 1,000 and 300,000 photons per second (i.e., 1 and 300 kHz). Although, persons of ordinary skill in the art will appreciate that higher or lower counts may be used.

In an FCS system with a sample of material (biological, chemical, pharmaceutical, or otherwise) on the substrate 106, an FCS detection volume is formed in the evanescent field 122. The FCS detection volume is a confocal region in the material that is characterized by a Rayleigh range or depth of focus and a beam waist. This depth of focus may be thought of as the conjugate of the focal plane formed through a pinhole, meaning that fluorescent light collected over this range by the objective 116 would be focused onto a pinhole and any light coming from above or below this region would be filtered out. The size of the confocal region (or detection volume) may be defined by the objective 116 and the size of the optical input to the photodetector 130, which may be a 200 μm core optical fiber. It is also noted that the term confocal region as used herein refers to at least a portion of the affected volume of material, i.e., the volume over which fluorescence occurs. The techniques described herein may result in a reduction in this affected region from that of conventional systems, such that less sample fluoresces during illumination. Further, the confocal region may also be reduced, over conventional systems, such that a smaller sample volume is measured.

Figure 5:
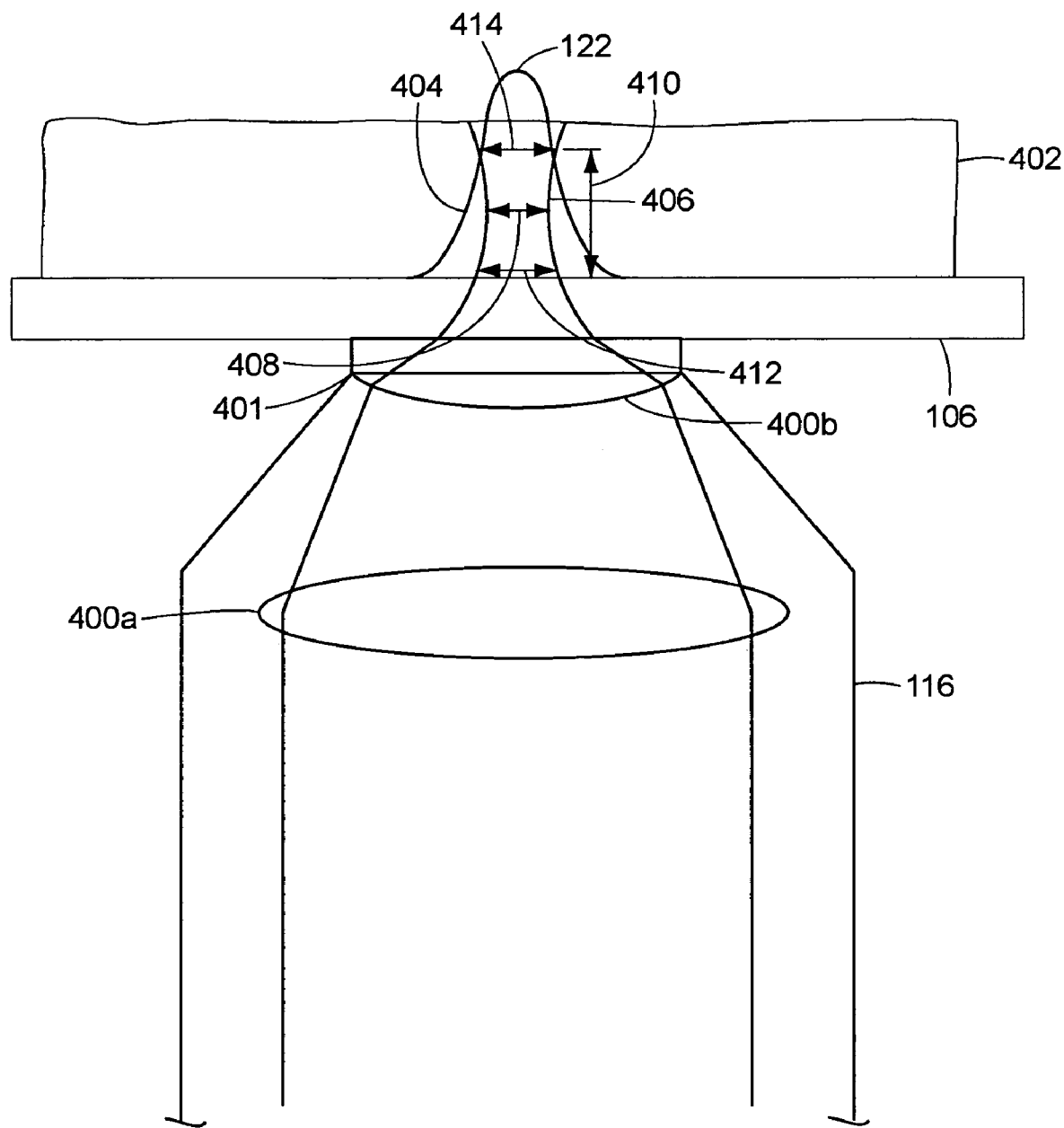
FIG. 5 illustrates an example evanescent field and confocal region formed in a sample of a material.

FIG. 5 illustrates the evanescent field 122 formed by focusing the annular illumination beam 112 through the high numerical aperture objective 116, which includes two focusing lenses 400a and 400b and an immersion buffer 401 or index matching region, in the illustrated example. The evanescent field 122 (shown with an example profile) extends into a sample of material 402 positioned on the optical substrate 106. The material, which may be a biological, chemical, pharmaceutical or other, may be attached to the substrate 106 through known techniques, some of which are described further below. The focused beam 112 forms an affected region 404 in the evanescent field 122, the affected region 404 being the region of the evanescent field 122 over which material within the sample 402 may fluoresce.

A confocal region 406 measured by the objective 116 is generally represented by a volume bounded in an XY plane (i.e., into the drawing) by a beam waste diameter 408 and bounded in a Z direction by a height 410. In the illustrated example, the height 408 extends from a first beam waist 412 to a second beam waist 414. The height 408 represents the penetration depth of the confocal region 404 into the sample 402 and is less than that achievable with conventional FCS techniques. The penetration depth 410 may be approximately 1000 nm or less and, in some specific examples, may be between 50 nm and 200 nm. In the example of nano-complex biological materials in the sample 402, the penetration depth may be on the scale of the biological material, i.e., 100 nm or below, for example.

Furthermore, in some examples the penetration depth is tunable to different heights, for example, to achieve a desired signal to noise ratio. The tuning may be achieved by adjusting the parameters of the hologram or the phase mask component of the DOE to alter the inner diameter of the primary ring of the annular illumination beam, for example. In an FCS system, a computer may collect fluorescence data based on a first penetration depth and characterized by a first signal to noise ratio. The operator may then determine whether this signal to noise ratio is acceptable and, if not, correspondingly adjust the penetration depth until an acceptable or desired signal to noise ratio is achieved. Thus, the present techniques may not only form a confocal region 406 that has a smaller penetration depth than conventional systems, this penetration depth may be adjustable.

An FCS implementation is now described by way of example, not limitation.

Example FCS Implementation

The reference beam from the Coherent Sapphire 488 nm-20 mW blue laser was focused onto a diffraction-limited spot in a bacterium sample using an illumination apparatus as described above. The green emitted fluorescence from the excited region of the bacterium sample was collected with a confocal detection system that included a photon counting module (e.g., a SPCM-AQR-16FC, a single photon counting module operating over a range of 400 nm to 1060 nm at 25 black current counts per second, available from Perkin-Elmer of Wellesley, Mass.) that monitored photon events associated with the free diffusion of fluorescent particles in the detection volume. Fluorescent labeled latex beads (e.g., G40 fluorescent polymer microspheres, available from Duke Scientifics Corp. or Palo Alto, Calif.) were used to characterize the effect of the annular illumination in FCS measurements. The collected green fluorescence was coupled into an optical fiber receptacle for the photon counter and was analyzed in real-time using a fast correlator coupled to the computer via a PC-expansion board (e.g., an ALV 5000EPP fast correlator from AVP-Laser-Vertriebsgesellschaft mbH of Largen/Hessen Germany). With the fluorescence measured, the temporal fluctuations of the fluorescence intensity of the fast correlator were characterized using a linear multi-channel counting board (i.e., the MCS32 PCI-based counting board, from Ortec Corporation of Oak Ridge, Tenn.) or an ALV5000 fast correlator (from AVP-Laser-Vertriebsgesellschaft mbH). The associated autocorrelation function was calculated to determine biological function that affected diffusion time and/or concentration.

The temporal variations detected at the fast correlator arose from the fluorescent molecules diffusing in and out the confocal region, i.e., in and out of the FCS detection volume, including along the Z axis. The fewer the diffusing molecules, the larger the fluctuations would be about the mean fluorescence signal. Because, the example technique relied upon fluctuations and not on the absolute value of the fluorescence signal, the measure of concentrations and diffusion constants was self-calibrating.

A mathematical analysis of these fluctuations was achieved to determine biological functions, such as the binding affinity between biological materials within the bacterium sample and the ratio of bound molecules in the bacterium sample to free molecules. The amplitude of the autocorrelation function at the intercept with the vertical axis was determined to be inversely equal to the number of molecules (N) in the detection volume. The autocorrelation functions associated with the conventional Gaussian laser illumination were given by:

$$G(\tau) = \left(\frac{1}{N}\right)\left(1 \frac{1}{\left(1+\frac{t}{\tau}\right)}\right) \quad (4)$$

where N was the number of molecules in the confocal volume and τ was the diffusion time associated with the free diffusing fluorescent molecules. In order to characterize the autocorrelation function G(τ) associated with the present total internal reflection FCS technique, the following model was used:

$$G(t) = \frac{1}{2N}\left(1+\frac{t}{\tau_{xy}}\right)^{-1}\left[\left(1-\frac{t}{2\tau_z}\right)\omega\left(i\sqrt{\frac{2}{4\tau_z}}\right) + \sqrt{\frac{t}{\pi\tau_z}}\right] \quad (5)$$

with $\tau_z = z^2/4D$, $\tau_{xy}$ was the lateral diffusion time and N the number of beads in the excitation volume $N = \pi R^2 z \, C_{beads}$, where $C_{beads}$ was the beam concentration, where z was the penetration-depth of the evanescent wave and R was the radius of the beam, and where D was the diffusion constant. Both illuminations, the annular illumination beam and the conventional beam profile, produced a diffraction limited spot with similar XY dimensions. It is noted that the XY dimension of the diffraction spot created by the annular illumination beam may be decreased even further, e.g., by a factor of 3, using a radial instead of a linear polarization, where such a modification would increase the XY resolution of the diffracted laser spot. Although the XY dimensions were similar, the penetration depth dimensions of the two were noticeably different.

Figure 6:
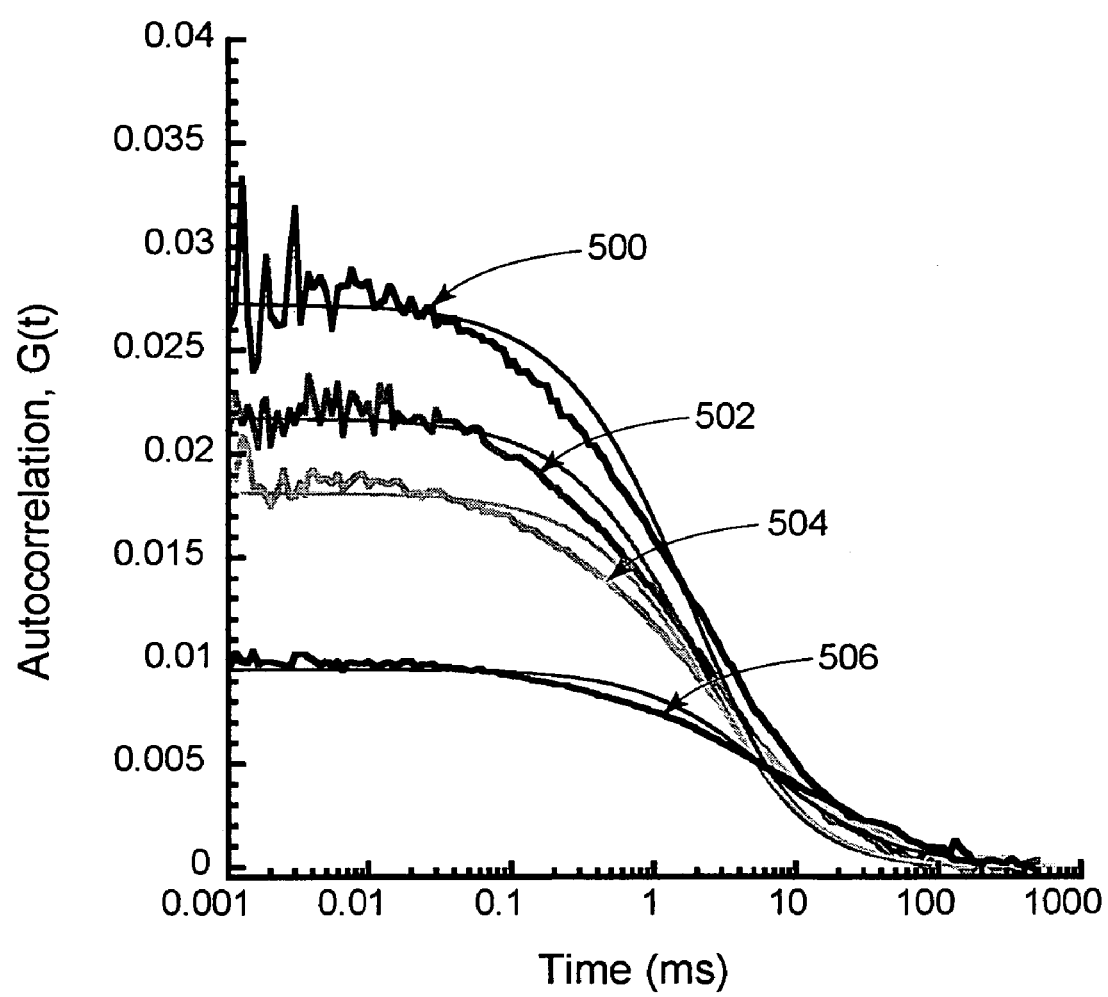
FIG. 6 illustrates autocorrelation curves for incident beam profiles of different dimensions.

FIG. 6 plots autocorrelation curves obtained from free diffusing fluorescent beads (d=44 nm) for different annulus diameters. Curve 500 corresponds to an annular diameter of 9.3 mm, curve 502 corresponds to a diameter of 8.9 mm, and curve 504 corresponds to a diameter of 8.7 mm. These curves 500, 502, and 504 represent annular beams focused for TIR. The corresponding thin line shown for each curve is a fit curve obtained from equation (2). $\tau_z = (z^2/4D)$ and N were the fit parameters (D was the diffusion constant, z the penetration depth). $\tau_{xy}$ was fixed at 2.4 ms. The penetration depth varied from 150 nm to 300 nm. The curve 506 shows a typical behavior of a classical FCS measurement.

From the decay times of the profiles of curves 502-504, it was apparent that the diffusion time had decreased by a factor of ten. The smaller decay time demonstrated that a smaller confocal volume was excited, which meant the FCS could be measured with a better signal to noise ratio.

As a result of the improved diffusion time results and better resolution, we found that the penetration depth associated with the annular illumination beam was about 150 nm and the FCS detection volume approximately ten times smaller than that of conventional FCS, in this example. It is noted that the penetration depth is directly related to the angle of illumination and the differences in indexes of the two media. This penetration depth is given by the formula:

$$d = \frac{\lambda}{4\pi}[n_1^2\sin^2(\theta) - n_2^2]^{-1/2} \quad (6)$$

with $n_1$ being the refractive index of the optical glass substrate (e.g., $n_1 = 1.51$), $n_2$ being the refraction index of the solution (e.g., usually aqueous solution $n_2 = 1.33$) and θ being the angle of incidence of the illumination beam. We estimated θ=63.4° using the measured penetration depth (150 nm) and the equation (6). Under these conditions (with the objective lens having a NA=1.45), the critical angle was 61.7° and the maximal incidence angle was 73.7°.

As noted above, it is possible to affect the penetration depth by adjusting several specific parameters. The parameter $\rho_0$ of the phase mask equations (2) and (3) above controls the size of the dark core of the Bessel profile beam. As the value of $\rho_0$ increases, the size of the dark core of the annular illumination beam increases as well, which effect (or the converse thereof) may be used to tune the penetration depth of the confocal region. It is also noted that as the distance of propagation is lengthened, the magnitude of laser power in the annular illumination beam of the diffraction pattern increases. Thus, as the beam travels farther from the DOE, the annular illumination becomes sharper.

Figure 7:
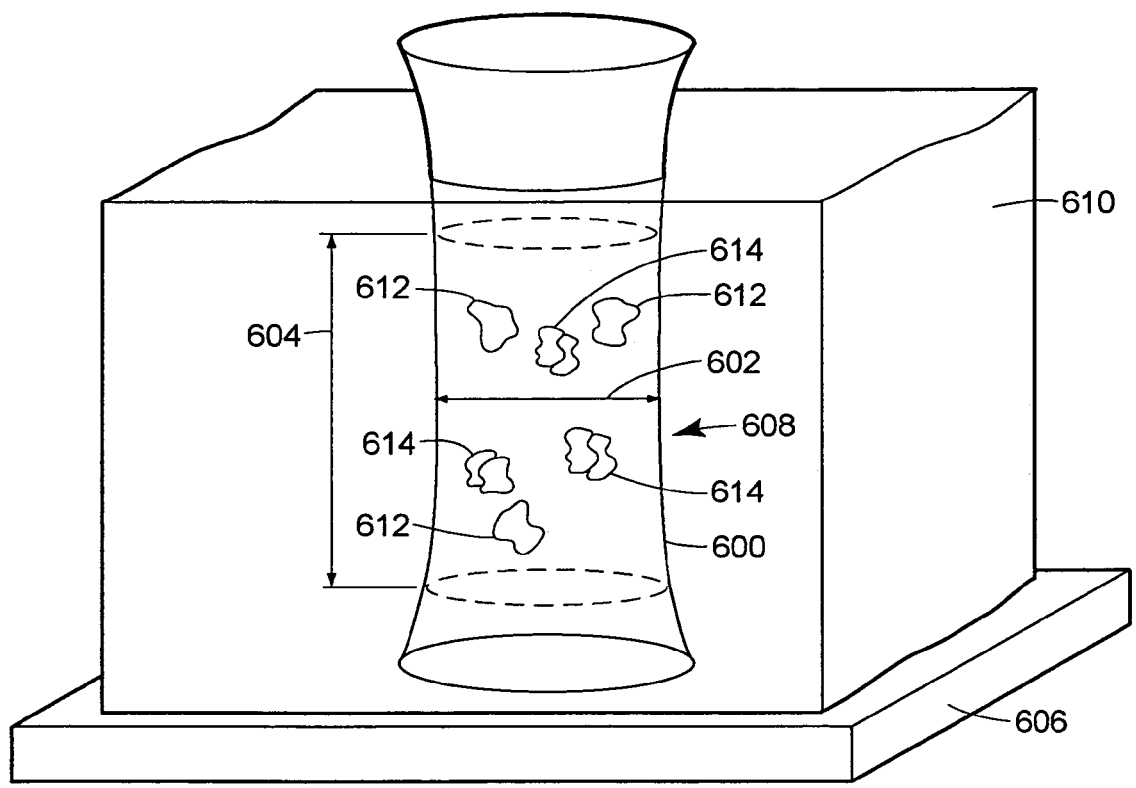
FIG. 7 illustrates a confocal region formed by an imaging apparatus according to an example and having free molecules and bound molecules.

FIG. 7 illustrates an example confocal region 600 having a diameter width 602 and a penetration depth 604 extending above the substrate 606. The confocal region 600 overlaps a portion 608 of a sample material 610 that has free molecules 612 and bound molecules 614. The FCS techniques described above may measure biological function of the bound molecules 614 over the confocal region 600, such as binding affinity or the ratio of bound/free molecules.

In the example of a biological material as the sample 610, the biological material may be any material from which fluorescence is to be detected. The biological material may be a lipid, a small molecule, a protein, an antibody, a receptor and the like. Alternatively, the biological material may be a whole cell, such as a bacterial cell, plant cell, animal cell, virus or the like. In yet other alternatives, the biological material may be an organelle from a cell. The biological material may be disposed on a solid substrate such as for example a glass surface, a test tube, and the like. The material may be a protein, a nucleic acid, a synthetic small molecule organic compound, a lipid, an antibody and the like. Proteins may include receptors, protein ligands for such receptors, antibodies, and the like. For example, an antibody region may be immunologically reactive with a non-protein binding partner such as a lipid or other organic compound. Preferably, the biological material is disposed on a surface in an organizational fashion that allows the detection and determination of identity of the specific biological material at a given location on the solid surface. Either the protein or its binding partner is displayed on the solid support.

The biological materials may be bound to a solid substrate in a microarray format. Microarray chips are well known to those of skill in the art (see, e.g., U.S. Pat. Nos. 6,308,170; 6,183,698; 6,306,643; 6,297,018; 6,287,850; 6,291,183, each incorporated herein by reference). These are exemplary patents that disclose nucleic acid microarrays and those of skill in the art are aware of numerous other methods and compositions for producing microarrays comprising nucleic acids or proteins.

DNA- and RNA-based microarrays provide a simple way to explore the expression of gene expression in a sample for diagnostic purposes, and for screening of novel sequences. Microarray chips are well known to those of skill in the art (see, e.g., U.S. Pat. Nos. 6,308,170; 6,183,698; 6,306,643; 6,297,018; 6,287,850; 6,291,183, each incorporated herein by reference). These are exemplary patents that disclose nucleic acid microarrays and those of skill in the art are aware of numerous other methods and compositions for producing microarrays which may be used in conjunction with the fluorescence, detection techniques described herein.

In terms of nucleic acid microarrays, the term "microarray" refers to an ordered arrangement of hybridizable array elements. In terms of protein microarrays, the term "microarray" refers to an ordered arrangement of peptides (e.g., ligands; receptors; antibodies and the like) as array elements. The array elements are arranged so that there are preferably at least two or more different array elements, more preferably at least 100 array elements, and most preferably at least 1,000 array elements, on a 1 $cm^2$ substrate surface. The fluorescence signal from each of the array elements is preferably individually distinguishable.

The microarray can be used for large scale genetic or gene expression analysis of a large number of target array elements. The microarray can also be used in the diagnosis of diseases and in the monitoring of treatments. Further, the microarray can be employed to investigate an individual's predisposition to a disease. Furthermore, the microarray can be employed to investigate cellular responses to infection, drug treatment, and the like.

When the composition of the biological material is employed as array elements in a microarray, the array elements may be organized in an ordered fashion so that each element is present at a distinguishable, and preferably specified, location on the substrate. In the some examples, because the array elements are at specified locations on the substrate, the hybridization patterns and intensities (which together create a unique expression profile) can be interpreted in terms of expression levels of particular genes and can be correlated with a particular disease or condition or treatment.

The composition comprising a plurality of polynucleotide array elements can also be used to purify a subpopulation of mRNAs, cDNAs, genomic fragments and the like, in a sample. Polypeptide array elements may likewise be used to asses the presence of biding partners of those polypeptides in a given sample. Typically, samples being tested will include target polynucleotides or binding partners of polypeptides of interest and other components which may interfere with the detection background; therefore, it may be advantageous to remove these polynucleotides or polypeptides from the sample. One method for removing the additional nucleic acids is by hybridizing the sample containing target polynucleotides with immobilized polynucleotide probes under hybridizing conditions. Those nucleic acids that do not hybridize to the polynucleotide probes are removed and may be subjected to analysis or discarded. At a later point, the immobilized target polynucleotide probes can be released in the form of purified target polynucleotides.

The nucleic acid probes may be genomic DNA or cDNA or mRNA, or any RNA-like or DNA-like material, such as peptide nucleic acids, branched DNAs, and the like. The probes may be sense or antisense polynucleotide probes. Where target polynucleotides are double stranded, the probes may be either sense or antisense strands. Where the target polynucleotides are single stranded, the probes are complementary single strands.

In some examples, the probes are cDNAs. The size of the DNA sequence of interest may vary and is preferably from 100 to 10,000 nucleotides, more preferably from 150 to 3,500 nucleotides.

The probes can be prepared by a variety of synthetic or enzymatic schemes, which are well known in the art. The probes may be synthesized, in whole or in part, using chemical methods well known in the art (Caruthers et al., Nucleic Acids Res., Symp. Ser., 215-233, 1980). Alternatively, the probes can be generated, in whole or in part, enzymatically.

Nucleotide analog can be incorporated into the probes by methods well known in the art. The only requirement is that the incorporated nucleotide analog must serve to base pair with target polynucleotide sequences. For example, certain guanine nucleotides may be substituted with hypoxanthine, which base pairs with cytosine residues. However, these base pairs are less stable than those between guanine and cytosine. Alternatively, adenine nucleotides can be substituted with 2,6-diaminopurine, which can form stronger base pairs than those between adenine and thymidine.

Additionally, the probes may include nucleotides that have been derivatized chemically or enzymatically. Typical chemical modifications include derivatization with acyl, alkyl, aryl or amino groups.

The polynucleotide probes can be immobilized on a substrate. Preferred substrates are any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which the polynucleotide probes are bound. Preferably, the substrates are optically transparent.

Complementary DNA (cDNA) can be arranged and then immobilized on a substrate. The probes can be immobilized by covalent means such as by chemical bonding procedures or UV exposure. In one such method, a cDNA is bound to a glass surface which has been modified to contain epoxide or aldehyde groups. In another case, a cDNA probe is placed on a polylysine coated surface and then UV cross-linked (Shalon et al., PCT publication WO95/35505, herein incorporated by reference). In yet another method, a DNA is actively transported from a solution to a given position on a substrate by electrical means (Heller et al., U.S. Pat. No. 5,605,662). Alternatively, individual DNA clones can be gridded on a filter. Cells are lysed, proteins and cellular components degraded, and the DNA coupled to the filter by UV cross-linking.

Furthermore, the probes do not have to be directly bound to the substrate, but rather can be bound to the substrate through a linker group. The linker groups are typically about 6 to 50 atoms long to provide exposure to the attached probe. Preferred linker groups include ethylene glycol oligomers, diamines, diacids and the like. Reactive groups on the substrate surface react with one of the terminal portions of the linker to bind the linker to the substrate. The other terminal portion of the linker is then functionalized for binding the probe.

The probes can be attached to a substrate by dispensing reagents for probe synthesis on the substrate surface or by dispensing preformed DNA fragments or clones on the substrate surface. Typical dispensers include a micropipette delivering solution to the substrate with a robotic system to control the position of the micropipette with respect to the substrate. There can be a multiplicity of dispensers so that reagents can be delivered to the reaction regions simultaneously.

In these examples, the substrate may be positioned in the evanescent field extending above the substrate within which TIR occurs from focusing of the annular illumination beam or alternatively such total internal reflection may occur within the substrate upon which the material is bound.

In addition to microarrays, the present detection techniques also may be used in the analysis of phage display libraries. Phage display uses bacteria and bacterial viruses known as phage to produce and select synthetic antibodies that have all the target-recognition qualities of natural antibodies. Often, these synthetic antibodies are produced using the same genes that code for the target-recognition or variable region in natural antibodies from mammalian systems. The phage are genetically engineered so that a particular antibody is fused to a protein on the phage's coat and the gene encoding the displayed antibody is contained inside the phage particle. This technology thus couples the displayed antibody's phenotype to its genotype, allowing the DNA that codes for the selected antibody to be retrieved easily for future use. Collections of these antibody-covered phage are called a library. Phage libraries each typically contain a billion different antibodies, a number comparable to that in human immune systems.

To select the phage with the desired antibody from a library, the phage are allowed to bind to the target molecule, which is attached to a solid surface. The phage with antibodies that recognize the target molecule bind tightly, and the remaining (unbinding) phage are simply washed away. (Phage display even permits researchers to select antibodies with different binding characteristics for a given target.) The DNA contained within the desired phage then can be used to produce more of the selected antibody for use in research or medical diagnostics.

The techniques described herein may be used in fluorescence correlation spectroscopy systems that analyze these or other materials.

Figure 8:
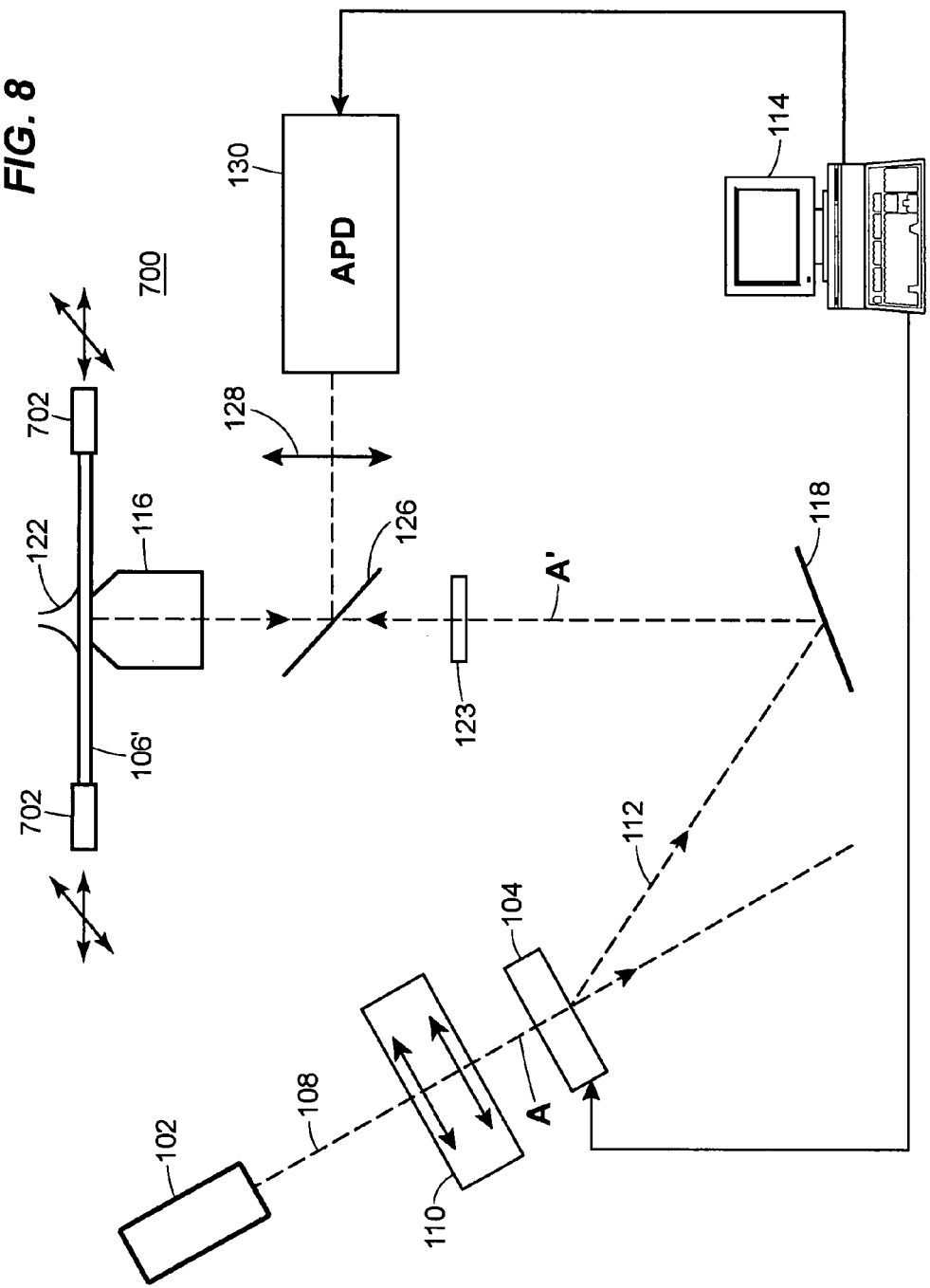
FIG. 8 illustrates an apparatus like that of FIG. 1, but for use in imaging a material.

Separately, the techniques may be used in other applications, such as in imagining systems (e.g., scanning microscopy systems) where fluorescence may be used to image a biological, chemical, pharmaceutical or other material. FIG. 8 illustrates an example imaging apparatus 700 having an illumination portion similar to that of apparatus 100, and thus bearing like reference numerals. However, in addition to the photon counter 130 the apparatus 700 includes an XY translation stage 702 (generally shown) coupled to the computer 114 for controlling the position of the substrate 106', in particular the position of the evanescent field 122 in a sample disposed on the substrate 106'. For example, under synchronized control of the computer 114, the translation stage may adjust the position of the substrate 106' in an XY plane thereby adjusting the region of the sample measured by the confocal region. The computer 114 can scan the substrate 106' such that a full two dimension area of the sample is scanned, and, under control of the photo counter 130, the apparatus 700 may count fluorescence photons over this scanned area. This fluorescence data may be provided to the computer 114 which may then perform counting analysis and signal processing on the data to develop an image of the sample on the substrate 106' for display on a video monitor.

Although certain apparatus constructed in accordance with the teachings of the invention have been described herein, the scope of coverage of this patent is not limited thereto. On the contrary, this patent covers all embodiments of the teachings of the invention fairly falling within the scope of the appended claims either literally or under the doctrine of equivalence.

What we claim is:

1. An illumination apparatus comprising:
a laser source for providing a reference laser beam;
a diffractive optical element positioned to receive the reference laser beam and convert the reference laser beam into an annular illumination beam; and
an optical objective positioned to couple the annular illumination beam into an optical substrate to produce an evanescent wave above the optical substrate.

2. The illumination apparatus of claim 1, wherein the diffractive optical element comprises a dynamically changeable diffractive component.

3. The illumination apparatus of claim 2, wherein the dynamically changeable diffractive component comprises a computer-generated hologram.

4. The illumination apparatus of claim 3, further comprising a liquid crystal component imprinted with the computer-generated hologram.

5. The illumination apparatus of claim 1, wherein the diffractive optical element is an adjustable spatial light modulator having an electrically-addressable phase mask component.

6. The illumination apparatus of claim 5, further comprising a controller coupled to the electrically-addressable spatial light modulator to adjust the phase mask component.

7. The illumination apparatus of claim 6, wherein the controller comprises a microcomputer.

8. The illumination apparatus of claim 5, wherein the phase mask component has a phase function given by:

$$\psi(\rho,\phi)=(\alpha\rho+n\phi+2\pi\upsilon\rho\cos\phi)\mod[\pi]$$

wherein $\alpha=(2\pi/p_0)$ and $\upsilon=\sin\gamma/\lambda$, wherein $\gamma$ is the angle between the reference laser beam and a line normal to a surface of the adjustable spatial light modulator, wherein $\lambda$ is the wavelength of the reference laser beam and n is the order number, and wherein $\rho$ and $\phi$ are cylindrical coordinates of the phase mask component.

9. The illumination apparatus of claim 8, wherein $\alpha$ is 2.8, n is 2 and $\upsilon$ is 0.25.

10. The illumination apparatus of claim 1, where the annular illumination beam has a Bessel profile having an order number that is at least two, and wherein the annular illumination beam has a primary annular ring with an outer diameter and an inner diameter.

11. The illumination apparatus of claim 10, wherein the order number is an even number.

12. The illumination apparatus of claim 1, wherein the optical objective has a numerical aperture of at least 1.4.

13. The illumination apparatus of claim 1, wherein the optical objective is positioned relative to the optical substrate to form an confocal region extending above the optical substrate and having a penetration depth of 1000 nm or below.

14. The illumination apparatus of claim 13, wherein the penetration depth is between 50 nm and 200 nm.

15. The illumination apparatus of claim 1, further comprising a photodetector positioned to detect fluorescence from a material.

16. The illumination apparatus of claim 15, wherein the photodetector is an avalanche photodiode apparatus.

17. The illumination apparatus of claim 15, further comprising a computer coupled to the photodetector for determining a fluorescence spectroscopy for the material.

18. The illumination apparatus of claim 17, further comprising a computer coupled to the photodetector for determining an image of the material.

19. For exciting a material disposed on an optical substrate, an apparatus comprising:
    a laser source for providing a reference laser beam;
    a optical element positioned to receive the reference laser beam and convert the reference laser beam into an annular illumination beam; and
    an optical objective having an axis substantially normal to an entrance face of the optical substrate, the optical objective positioned to focus the annular illumination beam into the optical substrate and to produce an evanescent wave having a confocal region with a penetration depth into the material of 1000 nm or less.

20. The apparatus of claim 19, wherein the optical element comprises a dynamically changeable diffractive optical component.

21. The apparatus of claim 20, wherein the dynamically changeable diffractive optical component comprises a computer-generated hologram.

22. The apparatus of claim 21, further comprising a liquid crystal component imprinted with the computer-generated hologram.

23. The apparatus of claim 19, wherein the optical element is an adjustable spatial light modulator having an electrically-addressable phase mask component.

24. The apparatus of claim 23, wherein the phase mask component has a phase function given by:

$$\psi(\rho,\phi)=(\alpha\rho+n\phi+2\pi\upsilon\rho\cos\phi)\mod[2\pi]$$

wherein $\alpha=(2\pi/\rho_0)$ and $\upsilon=\sin\gamma/\lambda$, wherein $\gamma$ is the angle between the reference laser beam and a line normal to a surface of the adjustable spatial light modulator, wherein $\lambda$ is the wavelength of the reference laser beam and n is the order number, and wherein $\rho$ and $\phi$ are cylindrical coordinates of the phase mask component.

25. The apparatus of claim 24, wherein $\alpha$ is 2.8, n is 2 and $\upsilon$ is 0.25.

26. The apparatus of claim 19, wherein the optical objective has a numerical aperture of at least 1.4.

27. The apparatus of claim 19, wherein the penetration depth is between 50 nm and 200 nm.

28. The apparatus of claim 19, wherein the annular illumination beam has a Bessel profile having an order number that is at least two, and wherein the annular illumination beam has a primary annular ring with an outer diameter and an inner diameter.

29. A method of exciting fluorescence in a material, the method comprising:
    coupling a reference laser beam into a diffractive optical element to convert the reference laser beam into an annular illumination beam propagating along an axis;
    focusing the annular illumination beam onto an optical substrate via an optical objective aligned along the axis;
    forming an evanescent field extending above the optical substrate, the evanescent field forming an affected region; and
    forming a confocal region in the affected region, the confocal region having a penetration depth extending into a sample of the material positioned at an exit face of the optical substrate.

30. The method of claim 29, further comprising coupling the reference laser beam into a dynamically changeable diffractive optical component.

31. The method of claim 30, wherein the dynamically changeable diffractive optical component comprises a computer-generated hologram.

32. The method of claim 31, wherein the dynamically changeable diffractive optical component comprises a liquid crystal component imprinted with the computer-generated hologram.

33. The method of claim 32, further comprising coupling the reference laser beam into an adjustable spatial light modulator having an electrically-addressable phase mask component.

34. The method of claim 33, wherein the adjustable spatial light modulator is a computer-addressable spatial light modulator, the method further comprising:
    coupling a computer to the computer-addressable spatial light modulator; and
    executing instructions on the computer to set the phase mask component of the computer-addressable spatial light modulator.

35. The method of claim 29, wherein the annular illumination beam has a Bessel profile having an order number that is at least two, and wherein the annular illumination beam has a primary annular ring with an outer diameter and an inner diameter.

36. The method of claim 35, further comprising varying the inner diameter of the annular illumination beam to tune the penetration depth of the confocal region.

37. The method of claim 36, further comprising tuning the penetration depth between approximately 50 nm to approximately 200 nm.

38. The method of claim 29, wherein the optical objective has a numerical aperture of at least 1.4.

39. The method of claim 29, further comprising polarizing the annular illumination beam to have a TM polarization.

40. A method of measuring a biological function of an affected region of a material disposed on an optical substrate, the method comprising:

coupling a reference laser beam into a diffractive optical element;

converting the reference laser beam into an annular illumination beam propagating along an axis;

focusing the annular illumination beam onto the optical substrate via an optical objective aligned along the axis;

forming an evanescent field extending above the optical substrate, the evanescent field forming the affected region;

forming a confocal region in the affected region, the confocal region having a penetration depth extending into the material;

collecting fluorescence from the confocal region; and correlating the fluorescence collected from the confocal region with the biological function of the material and providing an output representative of the correlation, thereby measuring the biological function of the material.

41. The method of claim 40, further comprising coupling the reference laser beam into a dynamically changeable diffractive optical component.

42. The method of claim 41, wherein the dynamically changeable diffractive optical component comprises a computer-generated hologram.

43. The method of claim 42, wherein the dynamically changeable diffractive optical component comprises a liquid crystal component imprinted with the computer-generated hologram.

44. The method of claim 40, further comprising coupling the reference laser beam into an adjustable spatial light modulator having an electrically-addressable phase mask component.

45. The method of claim 40, wherein the annular illumination beam has a Bessel profile beam having an order number that is at least two, and wherein the annular illumination beam has a primary annular ring with an outer diameter and an inner diameter.

46. The method of claim 45, further comprising varying the inner diameter of the annular illumination beam to tune the penetration depth of the evanescent wave.

47. The method of claim 46, further comprising tuning the penetration depth between approximately 50 nm and approximately 200 nm.

48. The method of claim 40, wherein the material comprises a base molecular component and a binding partner component, wherein the biological function is a binding affinity of the base molecular component to the binding partner component.

49. The method of claim 48, wherein the biological function changes a diffusion time of the base molecular component.

50. The method of claim 40, wherein the material comprises bound molecules and free molecules, and wherein the correlating comprises obtaining a ratio of bound molecules to free molecules within the material.

51. The method of claim 50, wherein the bound molecules are presented as a microarray.

52. The method of claim 51, wherein the microarray is a nucleic acid microarray.

53. The method of claim 52, wherein the nucleic acid microarray is selected from the group consisting of an RNA microarray and a DNA microarray.

54. The method of claim 51, wherein the microarray is a peptide micro array.

55. The method of claim 54, wherein the microarray comprises an array of receptors and wherein the free molecules are ligands for the receptors.

56. The method of claim 54, wherein the microarray comprises an array of ligands and wherein the free molecules are receptors for the ligands.

57. The method of claim 51, wherein the microarray is an antibody microarray.

58. The method of claim 50, wherein the bound molecules are provided as a phage display library.

59. A method of measuring a biological function of a material, the method comprising:

forming an annular illumination beam propagating along an axis;

focusing the annular illumination beam into an optical substrate;

forming an evanescent wave extending above the optical substrate, the evanescent wave forming an affected region;

forming a confocal region in the affected region and with a penetration depth into the material of 1000 nm or below;

collecting fluorescence from the confocal region; and correlating the fluorescence from the confocal region with the biological function of the material and providing an output representative of the correlation, thereby measuring the biological function of the material.

60. The method of claim 59, wherein forming the annular illumination beam comprises coupling a reference laser beam into a dynamically changeable diffractive optical component.

61. The method of claim 60, wherein the dynamically changeable diffractive optical component comprises a computer-generated hologram.

62. The method of claim 61, wherein the dynamically changeable diffractive optical component comprises a liquid crystal component imprinted with the computer-generated hologram.

63. The method of claim 59, wherein forming the annular illumination beam comprises coupling a reference laser beam into an adjustable spatial light modulator having an electrically-addressable phase mask component.

64. The method of claim 59, further comprising tuning the annular illumination beam to tune the penetration depth of the evanescent wave to a value between 200 nm and 50 nm.

65. The method of claim 59, wherein the material comprises a base molecular component and a binding partner component, wherein the biological function is a binding affinity of the base molecular component to the binding partner component.

66. The method of claim 65, wherein the biological function changes a diffusion time of the base molecular component.

67. The method of claim 59, wherein the material comprises bound molecules and free molecules, and wherein the correlating comprises obtaining a ratio of bound molecules to free molecules within the material.

68. The method of claim 67, wherein the bound molecules are presented as a microarray.

69. The method of claim 68, wherein the microarray is a nucleic acid microarray.

70. The method of claim 69, wherein the nucleic acid microarray is selected from the group consisting of an RNA microarray and a DNA microarray.

71. The method of claim 68, wherein the microarray is a peptide microarray.

72. The method of claim 71, wherein the microarray comprises an array of receptors and wherein the free molecules are ligands for the receptors.

73. The method of claim 71, wherein the microarray comprises an array of ligands and wherein the free molecules are receptors for the ligands.

* * * * *

UNITED STATES PATENT AND TRADEMARK OFFICE
CERTIFICATE OF CORRECTION

PATENT NO. : 7,330,255 B2
APPLICATION NO. : 11/008002
DATED : February 12, 2008
INVENTOR(S) : Philippe Cluzel et al.

It is certified that error appears in the above-identified patent and that said Letters Patent is hereby corrected as shown below:

In the Claims:

At Column 17, line 61, "micro array" should be -- microarray --.

Signed and Sealed this

Nineteenth Day of August, 2008

JON W. DUDAS
*Director of the United States Patent and Trademark Office*